US011073522B2

United States Patent
Wood

(10) Patent No.: US 11,073,522 B2
(45) Date of Patent: Jul. 27, 2021

(54) STRUCTURAL VALIDATION OF VERY LONG CHAIN DICARBOXYLIC ACIDS

(71) Applicant: Lincoln Memorial University, Harrogate, TN (US)

(72) Inventor: Paul L. Wood, Sacramento, CA (US)

(73) Assignee: Lincoln Memorial University, Harrogate, TN (US)

( * ) Notice: Subject to any disclaimer, the term of this patent is extended or adjusted under 35 U.S.C. 154(b) by 57 days.

(21) Appl. No.: 15/969,940

(22) Filed: May 3, 2018

(65) Prior Publication Data

US 2019/0339277 A1     Nov. 7, 2019

Related U.S. Application Data

(63) Continuation-in-part of application No. 15/284,219, filed on Oct. 3, 2016, now abandoned.

(51) Int. Cl.
*G01N 33/574* (2006.01)
*G01N 33/92* (2006.01)

(52) U.S. Cl.
CPC . *G01N 33/57484* (2013.01); *G01N 33/57419* (2013.01); *G01N 33/57438* (2013.01); *G01N 33/92* (2013.01); *G01N 2560/00* (2013.01)

(58) Field of Classification Search
CPC ....... G01N 33/57484; G01N 33/57438; G01N 33/92; G01N 33/57419; G01N 2560/00; G01N 33/57488
See application file for complete search history.

(56) References Cited

U.S. PATENT DOCUMENTS

| | | | |
|---|---|---|---|
| 2,343,644 | A | 3/1944 | Cawley |
| 3,162,658 | A | 12/1964 | Baltes et al. |
| 4,156,095 | A | 5/1979 | Jevne et al. |
| 4,937,320 | A | 6/1990 | Vreeswijk et al. |
| 5,053,534 | A | 10/1991 | Cosgrove |
| 6,409,649 | B1 | 6/2002 | Reaney |
| 6,414,171 | B1 | 7/2002 | Reaney |
| 7,501,479 | B2 | 3/2009 | Ionescu et al. |

(Continued)

FOREIGN PATENT DOCUMENTS

| | | |
|---|---|---|
| EP | 2770328 | 8/2014 |
| WO | WO2006092689 | 9/2006 |

(Continued)

OTHER PUBLICATIONS

Higashi et al. (Simple and practical derivatization procedure for enhanced detection of carboxylic acids in liquid chromatography-electrospray ionization-tandem mass spectrometry, Journal of Pharmaceutical and Biomedical Analysis, 2010) (Year: 2010).*

(Continued)

*Primary Examiner* — Lyle Alexander
*Assistant Examiner* — Jean Caraballo-Leon
(74) *Attorney, Agent, or Firm* — Blanchard & Associates

(57) ABSTRACT

The structures of very long chain dicarboxylic acids from blood samples may be validated through chemical derivatization of the dicarboxylic functionality with 2-picolylamine before positive ESI mass spectroscopy analysis. Laboratory standards may be used to quantify the concentration of the selected very long chain dicarboxylic acid in a blood sample.

10 Claims, 2 Drawing Sheets

100

110 — Sequentially Derivatize the Dicarboxylic Acids from a Blood Sample with [$^2H_4$]-Taurine and Then With Trimethylsilyl Diazomethane 120 — Optionally Derivatize any Hydroxy Functional Groups with [$^2H_6$]acetic anhydride 130 — Analyze the Resulting Mixture with Negative ESI Mass Spectrometry 140 — Optionally Perform 110-130 with a Known Standard and Quantify the Blood Sample Concentration of the Desired Dicarboxylic Acid

(56) References Cited

U.S. PATENT DOCUMENTS

| | | | |
|---|---|---|---|
| 7,534,917 | B1 | 5/2009 | Ngo et al. |
| 8,013,088 | B2 | 9/2011 | Ionescu et al. |
| 2002/0019056 | A1* | 2/2002 | Shushan .............. G01N 33/82 436/129 |
| 2014/0224976 | A1 | 8/2014 | Goldman |
| 2015/0057461 | A1 | 2/2015 | Park et al. |
| 2015/0176041 | A1 | 6/2015 | Griffin et al. |
| 2015/0299802 | A1 | 10/2015 | Therianos et al. |

FOREIGN PATENT DOCUMENTS

| | | |
|---|---|---|
| WO | WO2007030928 | 3/2007 |
| WO | WO2007109881 | 10/2007 |
| WO | 2011011882 | 2/2011 |
| WO | WO2011011882 | 2/2011 |
| WO | WO2011110349 | 9/2011 |

OTHER PUBLICATIONS

Joo et al. (A rapid and highly sensitive UPLC-MS/MS method using pre-column derivatization with 2-picolylamine for intravenous and percutaneous pharmacokinetics of valproic acid in rats, Journal of Chromtography, 2013) (Year: 2013).*

Reis et al. "A Comparison of Five Lipid Extraction Solvent Systems for Lipidomic Studies of Human LDL", Journal of Lipid Research, 2013; 54(7); 1812-1824 (Year: 2013).*

Cruz ef al. "Improved Butanol-Methanol (BUME) Method by Replacing Acetic Acid for Lipid Extraction of Biological Samples", Lipids. Jul. 2016; 51(7):887-898 (Year: 2016).*

Perttula et al. "Evaluating Ultra-long-Chain Fatty Acids as Biomarkers of Colorectal Cancer Risk" Cancer Epidemiol Biomarkers Prev. 2016; 25 (8):1216-1223. (Year: 2016).*

Ritchie, et al., Low-serum GTA-446 anti-inflammatory fatty acid levels as a new risk factor for colon cancer, International Journal of Cancer, 2013, 355-362, 132:2.

Ritchie, et al., Metabolic system alterations in pancreatic cancer patient serum: potential for early detection, BMC Cancer, 2013, 416, 13.

Ritchie, et al., Pancreatic cancer serum biomarker PC-594: Diagnostic performance and comparison to CA 19-9, World Journal of Gastroenterol, 2015, 6604-6612, 21.

Ritchie, et al., Human serum-derived hydroxy long-chain fatty acids exhibit anti-inflammatory and anti-proliferative activity, J Exp Clin Cancer Res, 2011, 59, 30.

Senanayake, et al., Metabolic dysfuctions in multiple sclerosis: implications as to causation, early detection, and treatment, a case control study, BMC Neurol, 2015, 154, 15.

Ritchie et al., Reduction of novel circulating long-chain fatty acids in colorectal cancer patients is indenpendent of tumor burden and , BMC Gastroentrol, 2010, 140, 10.

Ritchie et al., Reduced levels of hydroxylated, polyunsaturated ultra long-chain fatty acids in the serum of colorectal cancer , BMC Med, 2010, 13, 8.

Kamga et al. "Quantitative Analysis of Long Chain Fatty Acids Present in a Type I Kerogen Using Electrospray Ionization Fourier Transform Ion Cyclotron Resonance Mass Spectrometry: Compared with BF3/MeOH Methylation/GC-FID", Journal of the American Society for Mass Spectrom, 2014; vol. 25, No. 5, pp. 880-890.

Otto et al. "A Comparison of plant and microbial biomarkers in grassland soils from the Prairie Ecozone of Canada", Organic Geochemistry, 2005, vol. 36, No. 3, pp. 425-448. Published online Dec. 8, 2004.

Rezanka. "Branched and very Long-Chain Dicarboxylic Acids from Equisetum Species", Phytochemistry, 1998, vol. 47, No. 8, pp. 1539-1543.

Jung et al. "A new family of very long chain a, o-dicarboxylic acids is a major structural fatty acyl component of the membrane lipids of Thermoanaerobacter ethanolicus 39E", Journal of Lipid Research, 1994, vol. 35, pp. 1057-1065.

Symonds et al. "Blood Tests for Colorectal Cancer Screening in the Standard Risk Population", Current Colorectal Cancer Reports, 2015, vol. 11, No. 6, pp. 397-407.

Wood. "Endogenous Anti-Inflammatory Very-Long-Chain Dicarboxylic Acids" Potential Chemopreventive Lipids, Metabolites, 2018, vol. 8, No. 4, 76, pp. 1-11.

Wood et al. "Reduced Plasma Levels of Very-Long-Chain Dicarboxylic Acid 28:4 in Italian and Brazilian Colorectal Cancer Patient Cohorts", Metabolites, 2018, vol. 8, No. 4, 91, pp. 1-8.

European Patent Office, Supplemental European Search Report, Form 1503 03.82; dated Aug. 18, 2020.

Li et al. "Improved LC-MS Method for the Determination of Fatty Acids in Red Blood Cells by LC-Orbitrap MS", Analytical Chemistry, Mar. 23, 2011; vol. 83, p. 3192-3198; p. 3192, abstract, right col. para 3, p. 3193, Figure 1, p. 3194, left col. para 2.

Patent Cooperation Treaty, International Search Report, Form PCT/ISA/220, dated Jul. 30, 2019.

* cited by examiner

STRUCTURAL VALIDATION OF VERY LONG CHAIN DICARBOXYLIC ACIDS

BACKGROUND

Cancer is a disease in which abnormal cells begin to divide without control and can potentially invade other tissues. Several minimally-invasive, serum-based tests have been developed to identify people who are at a higher risk of developing certain types of cancers, including kidney and colorectal cancer.

One such test involves non-targeted lipidomics analysis of blood serum from patients who have been diagnosed with cancer. The lipid extracts within the serum are monitored by mass spectrometry to determine whether the number of species within a specific molecular mass range change over a selected time duration. The test then attempts to correlate a change within the specific molecular mass range correlates to a cancerous state.

However, since many of the lipids of interest have yet to be synthesized as analytical standards, thus having molecular structures that are not definitively known, many such lipids have been conventionally mistaken for Vitamin E metabolites. Without the lipid candidates of interest having been synthesized as known analytical standards, and thus having known molecular weights and fragmentation behavior, it has been difficult to validate the structural assumptions of the lipids corresponding to the mass peaks determined by mass spectrometry. This has made it difficult to develop and improve the reliability of clinical assays for relying on lipid biomarkers to determine a cancerous or pre-cancerous state.

As can be seen from the above description, there is an ongoing need for simple and efficient methods to accurately identify and assign to the appropriate classes lipid biomarkers that may be used as early stage risk indicators for cancer. The materials and methods of present invention overcome at least one of the disadvantages associated with conventional techniques.

SUMMARY

In one aspect, the invention provides method of validating the molecular structure of very long chain dicarboxylic acids, the method includes combining a sample derived from blood with 2-picolamine to form a first mixture; and analyzing the first mixture with positive ion electrospray ionization mass spectrometry, where atomic mass peaks of approximately 90.058 amu are attributed to carboxylic acids and mass peaks from approximately 444 to 555 amu are attributed to a very long chain dicarboxylic acid.

In another aspect of the invention, the method further includes combining a known concentration of a synthesized dicarboxylic acid with the 2-picolamine to form a second mixture; analyzing the second mixture with the positive ion electrospray ionization mass spectrometry, where the atomic mass peaks of approximately 90.058 amu are attributed to carboxylic acids; and quantifying the very long chain dicarboxylic acids in the first mixture by comparing the first mixture analysis with the second mixture analysis.

Other methods, features and advantages of the invention will be, or will become, apparent to one with skill in the art upon examination of the following figures and detailed description. It is intended that all such additional methods, features, and advantages be included within this description, be within the scope of the invention, and be protected by the claims that follow. The scope of the present invention is defined solely by the appended claims and is not affected by the statements within this summary.

BRIEF DESCRIPTION OF THE FIGURES

The invention can be better understood with reference to the following drawings and description. The figures are not intended to accurately represent molecules or their interactions, emphasis instead being placed upon illustrating the principles of the invention.

DETAILED DESCRIPTION

Screening blood samples for low levels of specific very long-chain dicarboxylic hydrocarbon biomarkers has potential as a useful tool for early identification of cancer risk and as an indicator for additional cancer testing. Identifying a decrease in the blood concentration of very-long chain dicarboxylic acids (VLCDCAs) with from (1) 28 to 30 carbon atoms, from 0 to 1 hydroxy group, and from 1 to 4 double bonds or from (2) 32 to 36 carbon atoms, from 1 to 2 hydroxy groups, and from 1 to 4 double bonds have proven useful for such cancer risk screening. These VLCDCAs have molecular masses from approximately 444 to 555 atomic mass units (amu.).

Such an example VLCDCA having 28 carbon atoms and 4 double bonds with the first double bond appearing after 6 carbon atoms from the left (hereinafter identified as VLCDCA 28:4n6 has the formula (I):

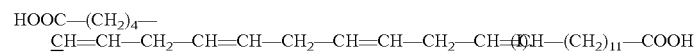

However, detecting these specific or structurally similar VLCDCAs, as opposed to other fatty acids in blood samples has proven difficult with conventional techniques.

Figure 1:
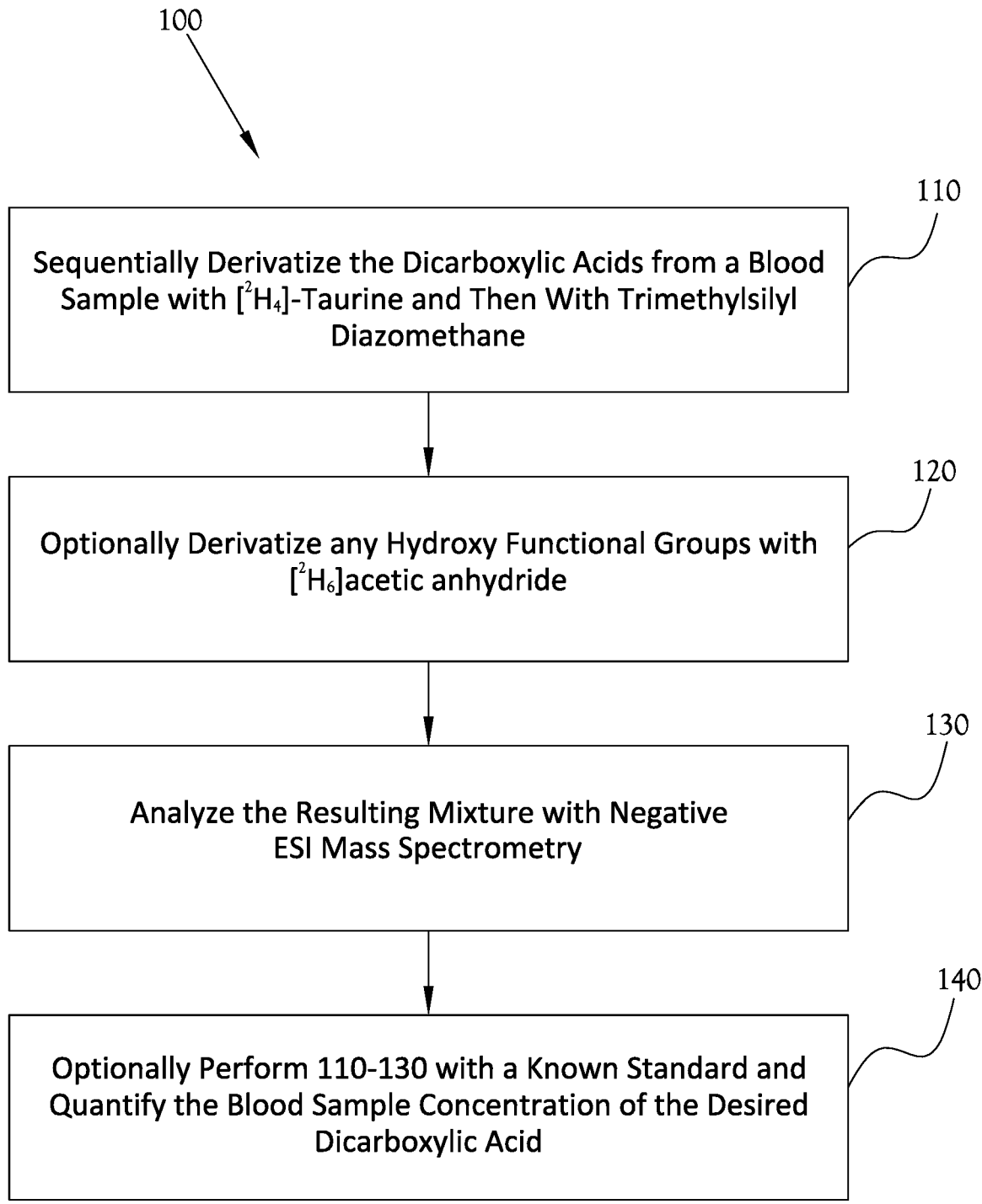
FIG. 1 represents a two-step derivatization negative ESI validation method.

FIG. 1 represents a two-step derivatization negative ESI validation method 100. In sequential, two-step validation 100, the structure of VLCDCA 28:4n6 was validated through [$^2$H$_4$]-Taurine and trimethylsilyl diazomethane chemical derivatization and subsequent negative electrospray (ESI) mass spectrometry. In derivatization 110, the dicarboxylic acids from blood serum are sequentially derivatized with [$^2$H$_4$]-Taurine and then with trimethylsilyl diazomethane. In optional hydroxy group derivatization 120, the hydroxy groups of dicarboxylic acids containing hydroxy functional groups may then be derivatized with [$^2$H$_6$]acetic anhydride.

In negative ESI analysis 130, the mixture is analyzed with negative ion ESI mass spectrometry to monitor the 571.3845 amu (446.33960 VLCDCA 28:4n6+111.02931 [$^2$H$_4$]-Taurine+14.01565 trimethylsilyl diazomethane) product as an ion of 570.3772 amu. The mixture also may be analyzed to monitor the 809.5896 amu (594.48594 VLCDCA 36:2+111.02931+14.01565+2*45.02939 acetic anhydride) product as an anion of 808.5824 amu.

In optional quantification 140, a known quantity of an internal standard, such as [$^2$H$_{28}$]VLCDCA 26:0, may be sequentially derivatized as in 110 and optionally as in 120 with monitoring of the 439.4351 amu product (314.39016 VLCDCA 26:0+111.02931+14.01565) as an ion of 438.4278 amu. during analysis 130 or in an independent ESI analysis. The known concentration of the internal standard may be used during the mass spectrometry analysis or in a second analysis to provide a baseline concentration for quantifying the naturally-occurring dicarboxylic acids in the blood sample.

Figure 2:
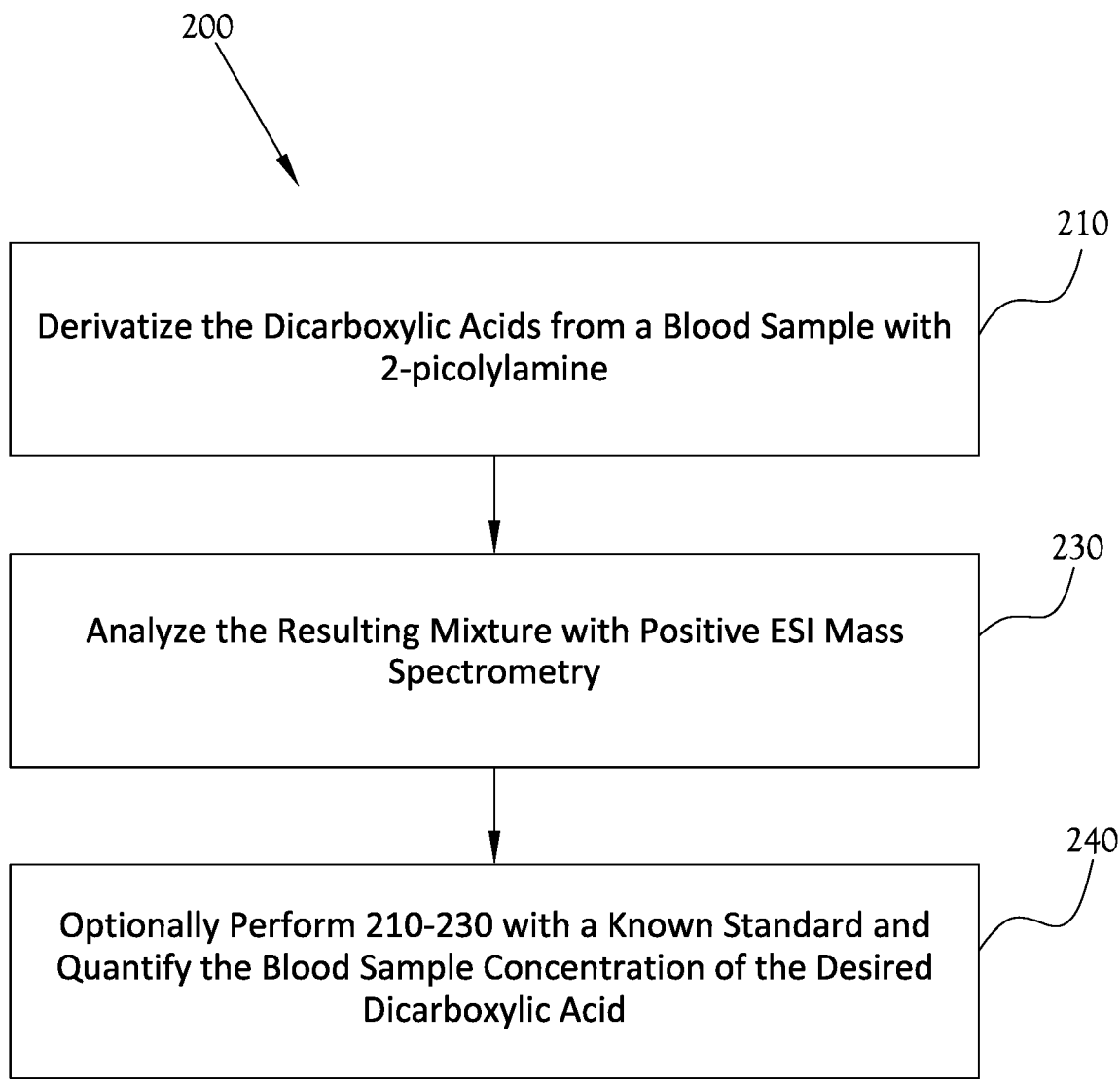
FIG. 2 represents a one-step derivatization positive ESI validation method.

FIG. 2 represents a one-step derivatization positive ESI validation method 200. In the validation 200, the structures of VLCDCA 28:4n6, VLCDCA 36:1, and VLCDCA 36:2 were validated through chemical derivatization with 2-picolylamine and subsequent positive electrospray mass spectrometry. In derivatization 210, the dicarboxylic acids are derivatized with 2-picolylamine.

In positive ESI analysis 230, the mixture is analyzed with positive ion ESI mass spectrometry where each carboxylic acid is identified as a cation through the addition of 90.058183 amu. per carboxylic functional group arising from 2-picolylamine. For example, the VLCDCA 28:4n6 having two carboxylic acid groups (446.3396 VLCDCA 28:4n6+2*90.05818 2-picolylamine=626.45596 amu) resulted in a 627.4632 amu (0.66 ppm mass error) calculated cation.

In optional quantification 240, a known quantity of an internal standard, such as [$^2$H$_{28}$]VLCDCA 16:0, may be derivatized as in 210 with monitoring of the 495.5138 amu product (314.3901 VLCDCA 16:0+2*90.05818 2-picolylamine) as an ion of 494.5065 amu. during analysis 230 or in an independent ESI analysis. The known concentration of the internal standard may be used during the mass spectrometry analysis or in a second analysis to provide a baseline concentration for quantifying the naturally-occurring dicarboxylic acids in the blood sample.

Numerous variations may be made to the following examples that lie within the scope of the invention.

EXAMPLES

Example 1: Preparation of a Dried Plasma Lipid Extract

A whole blood sample was obtained through venipuncture. The serum or EDTA plasma was isolated from the blood sample and stored in a low temperature environment. About 1 milliliter (mL) of methanol including approximately 1 nanomole of [$^2$H$_{28}$] dicarboxylic acid 16:0, approximately 1 mL of distilled water, and approximately 2 mL of tert-butyl methyl ether was added to approximately 100 microliters (uL) of the serum or EDTA plasma. The sample was agitated at high speed, such as with a Fisher Multitube Vortex, for approximately 30 minutes at room temperature. The upper organic layer including the lipid fraction was then allowed to separate by settling and decanted from the remaining aqueous layer. The organic layer was then dried by vacuum centrifugation. The [$^2$H$_{28}$] dicarboxylic acid 16:0 was obtained from CDN Isotopes, 88 Ave. Leacota, Pointe Claire, QC, H9R 1H1.

Example 2: Sequential Derivatization of Dicarboxylic Acid

To 1 milliliter (mL) of the dried plasma lipid extract of Example 1 was added 50 microliters (μL) of 2-chloro-1-methypyrinium iodide (15.2 mg per 10 milliliters of acetonitrile and 16.4 μL of trimethylamine). The sample was heated at 30° C. with shaking for 15 minutes, followed by the addition of 50 μL of [$^2$H$_4$]-Taurine (5 mg in 900 μL of distilled water and 100 μL of acetonitrile). Heating at 30° C. with shaking was continued for an additional 2 hours before the samples were dried by vacuum centrifugation. 100 μL of 2-propanol and 20 μL of trimethylsilyl diazomethane (2 M in hexane) was added and the sample again heated at 30° C. with shaking for 30 minutes. Next, 20 μL of glacial acetic acid was added to consume any remaining trimethylsilyl diazomethane. The sample was then dried by vacuum centrifugation prior to dissolution in a mixture of isopropanol, methanol, and chloroform (approximately 4:2:1) with the resulting mixture including an approximately 15 mM concentration of ammonium acetate.

If the dicarboxylic acid also includes hydroxy groups, after drying by vacuum centrifugation, but before dissolution in the mixture of isopropanol, methanol, and chloroform including ammonium acetate, the hydroxy groups may be derivatized with [$^2$H$_6$]acetic anhydride. This derivatization was performed by adding approximately 75 microliters of pyridine including the acetic anhydride to the dried sample. The samples were then heated at 60° C., with shaking, for 1 hour and dried by vacuum centrifugation prior to dissolution in the mixture of isopropanol, methanol, and chloroform containing the ammonium acetate.

Example 3: Negative Electrospray Mass Spectrometry

High resolution (e.g., 140,000 at 200 atomic mass unit) data acquisition, with sub-millimass accuracy, was performed on the sample via direct infusion with an orbitrap mass spectrometer, for example, of the type manufactured and sold by Thermo Scientific under the trademark "Q Exactive™". In embodiments in which multiple samples are processed according to the method, to minimize ghost effects from one sample to the next the input lines to the orbitrap mass spectrometer were washed using methanol and a mixture of hexane and ethyl acetate, in a ratio of approximately 3:2, respectively, between samples. After the negative ion electrospray ionization, the anions of dicarboxylic acid were quantitated, and from the acquired high-resolution dataset, the data was reduced to provide a listing of the analyzed VLCDCA/s in the blood sample/s.

Example 4: Synthesis of Synthetic Standard VLCDA 28:4n6

Utilizing the synthetic scheme of Li et al. (2005), ω-hydroxy-20:4n6-methyl ester was obtained by locking the required double bond positions relative to the ω-terminal of the target dicarboxylic acid. Next the alcohol was converted to a tetrahydropyranyl ether. With the ω-hydroxy group protected, the methyl ester was converted to an aldehyde. The carbon chain was extended by reacting the aldehyde with Grignard Reagent (ClMg—C$_8$H$_{16}$—OTHP). This derivative was subsequently de-protected and the 2 alcohol groups converted to carboxylic acids via Jones oxidation.

Example 5: Positive Electrospray Mass Spectrometry

The tandem mass spectra of the synthetic standard VLCDCA 28:4n6 as prepared in Example 4, and the organic extract of 3 mL of human plasma were compared. Three mL of human plasma was semi-purified via use of a basic anion exchanger (HyperSep Sax, Thermo Fisher). The column was conditioned by the sequential addition of 2 mL of methanol, 2 mL of water, and 2 mL of acetonitrile. The methanol-methyl-tert-butyl ether extract from 3 mL of human plasma was dried by vacuum centrifugation and re-dissolved in 2 mL of methanol which was applied to the conditioned column. The column was washed by the sequential addition of 2 mL of water, 2 mL of acetonitrile, and 2 mL of methanol. The dicarboxylic acids were then eluted with 2 mL of acetonitrile:methanol:formic acid (approximately 50:50:3). This eluate was then dried by vacuum centrifugation and dissolved in acetonitrile:methanol (approximately 1:1) for mass spectrometric analysis. The synthetic standard was dissolved in the same solvent.

The positive ion ESI spectra and the $MS^2$ spectra were obtained at high-resolution to assure high mass accuracy. The observed fragmentation supports the assignment of 2 terminal carboxylic acid functional groups and the positions of the double bonds.

Example 6: 2-Picolylamine Derivatization of Dicarboxylic Acid

Validation of the 2 carboxylic groups for VLCDCA 28:4n6, [$^2H_{28}$]VLCDCA 16:0, dihydroxy VLCDCA 36:2, and dihydroxy VLCDCA 36:1 was performed through derivatization with 2-picolylamine (PA) (Higashi et al., 2010]. To 3 mL of dried plasma lipid extracts, purified by anion exchange, was added 20 μL of triphenylphosphine (2.6 mg/mL acetonitrile), 20 μL of dithiopyridine (2.2 mg/mL acetonitrile), and 20 μL of 2-picolylamine (20 μL 2-picolylamine/mL acetonitrile). The samples were heated with shaking at 60° C. for approximately 10 minutes and then dried by vacuum centrifugation prior to dissolution in acetonitrile: methanol (approximately 1:1).

of acetonitrile, was added, and approximately 20 microliters of 2-picolylamine, at a concentration of approximately 15 microliters 2-picolylamine per milliliter of acetonitrile, was added. To maximize derivatization with the 2-picolylamine, the mixture was then heated while being agitated, for example by shaking (1400 rpm in an Eppenforf Thermomixer) at approximately 60° C. for approximately 10 minutes, and then dried by vacuum centrifugation. The mixture was then subjected to dissolution in a mixture of isopropanol, methanol, and chloroform, in ratios of 4:2:1, respectively, with the mixture including an approximately 15 mM concentration of ammonium acetate.

The positive ion ESI tandem mass spectrum of di-PA-VLCDCA 28:4n6 ($C_{40}H_{58}N_4O_2$) was dominated by 109.0760, the molecular cation for 2-picolylamine (PA, 1.9 ppm mass error). The next most prominent ion was 519.3945 ($C_{34}H_{50}N_2O_2$; [M+H-PA]$^+$; 2.3 ppm mass error) followed by 501.3839 ($C_{34}H_{48}N_2O_1$; [M+H-PA-$H_2O$]$^+$; 1.7 ppm mass error). The tandem [M+H-PA-$H_2O$]$^+$ ion has the potential to be very useful since this product ion is highly specific and can be monitored with high mass accuracy by either tandem quad-orbitrap or quad-TOF analysis.

The mass fragments for the serum and synthesized VLCDCA 28:4n6 is provided below in Table I. The table provides the calculated atomic mass units (amu) for the anion fragments with the mass error for the synthetic standard and the serum extract provided in parts per million (ppm).

TABLE I

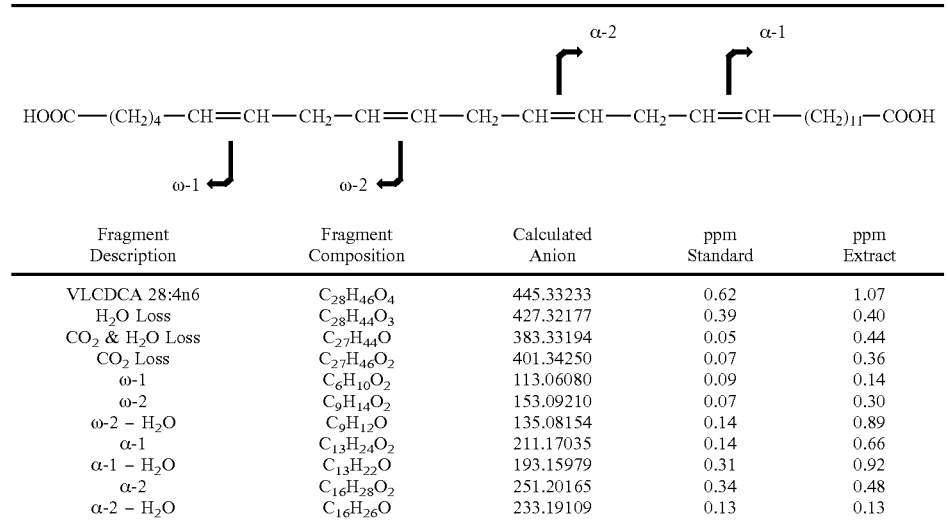

| Fragment Description | Fragment Composition | Calculated Anion | ppm Standard | ppm Extract |
|---|---|---|---|---|
| VLCDCA 28:4n6 | $C_{28}H_{46}O_4$ | 445.33233 | 0.62 | 1.07 |
| $H_2O$ Loss | $C_{28}H_{44}O_3$ | 427.32177 | 0.39 | 0.40 |
| $CO_2$ & $H_2O$ Loss | $C_{27}H_{44}O$ | 383.33194 | 0.05 | 0.44 |
| $CO_2$ Loss | $C_{27}H_{46}O_2$ | 401.34250 | 0.07 | 0.36 |
| ω-1 | $C_6H_{10}O_2$ | 113.06080 | 0.09 | 0.14 |
| ω-2 | $C_9H_{14}O_2$ | 153.09210 | 0.07 | 0.30 |
| ω-2 − $H_2O$ | $C_9H_{12}O$ | 135.08154 | 0.14 | 0.89 |
| α-1 | $C_{13}H_{24}O_2$ | 211.17035 | 0.14 | 0.66 |
| α-1 − $H_2O$ | $C_{13}H_{22}O$ | 193.15979 | 0.31 | 0.92 |
| α-2 | $C_{16}H_{28}O_2$ | 251.20165 | 0.34 | 0.48 |
| α-2 − $H_2O$ | $C_{16}H_{26}O$ | 233.19109 | 0.13 | 0.13 |

[$^2H_{28}$]VLCDCA 16:0: 314.3901+2*90.0582=494.5065→[495.5138]+, at 0.17 ppm mass error.

DH-VLCDCA 36:2: 594.4859+2*90.0582=774.6023→[775.6096]+, at 0.23 ppm mass error.

DH-VLCDCA 36:1: 596.5015+2*90.0582=776.6179→[777.6252]+, at 0.76 ppm mass error.

Validation of the two carboxylic groups for VLCDCA 28:4n6 also was obtained by derivatization of the carboxylic functional groups with 2-picolylamine as follows. Approximately 1 milliliter of dried lipid extract was added to approximately 20 microliters (μL) of triphenylphosphine the triphenylphosphine having a concentration of approximately 2.6 milligrams per microliter of acetonitrile. Approximately 20 microliters of dithiopyridine, at a concentration of approximately 2.2 milligrams dithiopyridine per microliter Unless the context clearly dictates otherwise, where a range of values is provided, each intervening value to the tenth of the unit of the lower limit between the lower limit and the upper limit of the range is included in the range of values.

While various aspects of the invention are described, it will be apparent to those of ordinary skill in the art that other embodiments and implementations are possible within the scope of the invention. Accordingly, the invention is not to be restricted except in light of the attached claims and their equivalents.

The invention claimed is:

1. A method of validating the number of carboxylic groups of a molecule identified through mass spectrometry as a potential very long chain dicarboxylic acid, the method comprising:

combining a sample for lipidomic analysis derived from blood of a patient who has been diagnosed with cancer with 2-picolylamine to form a first mixture; and analyzing the first mixture with positive ion electrospray ionization mass spectrometry, where mass peaks from approximately 444 to 555 amu are attributed to the presence of a potential very long chain dicarboxylic acid within the sample, where an amu increase of 2*90.058 amu over the approximately 444 to 555 amu mass peak of the potential very long chain dicarboxylic acid within the sample is attributed to derivatization of hydroxy groups in the potential very long chain dicarboxylic acid within the sample with 2-picolylamine, thereby validating that the potential very long chain dicarboxylic acid within the sample is a very long chain dicarboxylic acid, and where the potential very long chain dicarboxylic acid is chosen from molecules having 28 to 30 carbon atoms, from 0 to 1 non-dicarboxylic acid hydroxy groups, and from 1 to 4 carbon-carbon double bonds and from molecules having 32 to 36 carbon atoms, from 1 to 2 non-dicarboxylic acid hydroxy groups and from 1 to 4 carbon-carbon double bonds.

2. The method of claim 1, further comprising:

combining a known concentration of a synthesized dicarboxylic acid with the 2-picolylamine to form a second mixture;

analyzing the second mixture with the positive ion electrospray ionization mass spectrometry, where an amu increase of 2*90.058 over an amu of the synthesized dicarboxylic acid validates that the synthesized dicarboxylic acid includes two carboxylic acid functional groups; and quantifying the very long chain dicarboxylic acids in the first mixture by comparing the first mixture analysis with the second mixture analysis.

3. The method of claim 2, where the first mixture and the second mixture are simultaneously formed through combination with the 2-picolylamine.

4. The method of claim 2, where the first mixture and the second mixture are simultaneously analyzed with the positive ion electrospray ionization mass spectrometry.

5. The method of claim 1, where the first mixture includes acetonitrile and methanol in an approximately 1:1 ratio.

6. The method of claim 1, further comprising combining the sample with triphenylphosphine, dithiopyridine, and acetonitrile prior to the analyzing.

7. The method of claim 6, where the combining further comprises heating at approximately 60 degrees C.

8. The method of claim 1, where the validated very long chain dicarboxylic acid is selected from the group consisting of VLCDCA 28:4n6, DH-VLCDCA 36:2, DH-VLCDCA 36:1, and combinations thereof.

9. The method of claim 1, where the validated very long chain dicarboxylic acid is VLCDCA 28:4n6.

10. The method of claim 2, where the synthesized dicarboxylic acid is $[^2H_{28}]$VLCDCA 16:0.

* * * * *